(12) United States Patent
Kang et al.

(10) Patent No.: US 12,154,693 B2
(45) Date of Patent: Nov. 26, 2024

(54) STORE DEVICE FOR DIGITAL THERAPEUTIC OBJECT AND OPERATION METHOD THEREFOR

(71) Applicant: DAEGU GYEONGBUK INSTITUTE OF SCIENCE AND TECHNOLOGY, Daegu (KR)

(72) Inventors: Won Seok Kang, Daegu (KR); Chang Sik Son, Daegu (KR); Sang Hyeon Jin, Daegu (KR)

(73) Assignee: DAEGU GYEONGBUK INSTITUTE OF SCIENCE AND TECHNOLOGY [DGIST], Daegu (KR)

(*) Notice: Subject to any disclaimer, the term of this patent is extended or adjusted under 35 U.S.C. 154(b) by 498 days.

(21) Appl. No.: 17/713,334

(22) Filed: Apr. 5, 2022

(65) Prior Publication Data

US 2022/0392647 A1 Dec. 8, 2022

(30) Foreign Application Priority Data

May 26, 2021 (KR) .................. 10-2021-0067630
Nov. 26, 2021 (KR) .................. 10-2021-0165883

(51) Int. Cl.
*H04L 67/02* (2022.01)
*G16H 10/60* (2018.01)
*G16H 70/20* (2018.01)
*G16H 20/30* (2018.01)
*G16H 20/70* (2018.01)

(52) U.S. Cl.
CPC ............ *G16H 70/20* (2018.01); *G16H 10/60* (2018.01); *H04L 67/02* (2013.01); *G16H 20/30* (2018.01); *G16H 20/70* (2018.01)

(58) Field of Classification Search
None
See application file for complete search history.

(56) References Cited

U.S. PATENT DOCUMENTS

2007/0174196 A1* 7/2007 Becker ................... H04L 9/321
705/50
2007/0244904 A1* 10/2007 Durski ..................... G06F 8/30
2019/0243944 A1 8/2019 Jain et al.
(Continued)

FOREIGN PATENT DOCUMENTS

KR 10-2009-0078326 7/2009
KR 10-1336340 12/2013

OTHER PUBLICATIONS

Izrafin, "Day 34 Study: XML Parsing, DOM Parser", tistory, URL:https://myitis5212.tistory.com/38 (May 26, 2020). cited only pp. 1 to 6 (English translation pp. 1-6 only), total 31pages.
(Continued)

*Primary Examiner* — Craig C Dorais
(74) *Attorney, Agent, or Firm* — LEX IP MEISTER, PLLC

(57) ABSTRACT

Provided is a store device for digital therapeutic object including a processor, a storage unit configured to store a digital therapeutic object, and a memory electrically connected to the processor, at least one piece of code executed by the processor being stored in the memory, in which the memory stores the code causing the processor to process an XML-based DPR message requesting any one of registration, update of registration, abandonment of registration, usage, and abandonment of usage of the digital therapeutic object from a first external device.

18 Claims, 10 Drawing Sheets

(56) References Cited

U.S. PATENT DOCUMENTS

2021/0057057 A1    2/2021  Chin et al.
2021/0225512 A1*  7/2021  Himeno ................ G06F 16/245

OTHER PUBLICATIONS

National Institute of Medical Device safety Information, "Medical Device Standard Identification (UDI) Special Case Guidelines—Medical Device Software (SaMD), One-Set Medical Devices" (Dec. 2020), Cited only p. 4, (English translation p. 4 only), total 84 pages.

KIPO, Ofice Action of the corresponding Korean Patent Application No. 10-2021-0165883 dated Sep. 26, 2024, total 14 pages.

* cited by examiner

FIG. 6

```
<xml action="REGISTER or UPDATE", name="DIGITAL THERAPEUTICS_A">
    <DISEASE MANAGEMENT CODE>01011</DISEASE MANAGEMENT CODE>
    <LICENSE NUMBER>0010000</LICENSE NUMBER>
    <EXECUTION TERMINAL>
        <TERMINAL1 SPECIFICATION>···</TERMINAL1 SPECIFICATION>
        <TERMINAL2 SPECIFICATION>···</TERMINAL2 SPECIFICATION>
    </EXECUTION TERMINAL>
    <PURPOSE>···</PURPOSE>
    <EFFICACY>···</EFFICACY>
    <PRESCRIPTION METHOD>···</PRESCRIPTION METHOD>
    <PRECAUTIONS FOR USAGE>···</PRECAUTIONS FOR USAGE>
    <PRESCRIPTION_DIGITAL THERAPEUTICS>EXECUTION BINARY FILE</PRESCRIPTION_DIGITAL THERAPEUTICS>
</xml>
```

FIG. 7

```
<xml action="USE or ABANDON", name="DIGITAL THERAPEUTICS_A">
    <USER_IDENTIFICATION_ID>01010</USER_IDENTIFICATION_ID>
    <DISEASE MANAGEMENT CODE>01011</DISEASE MANAGEMENT CODE>
    <LICENSE NUMBER>0010000</LICENSE NUMBER>
    <EXECUTION TERMINAL>
        <TERMINAL2 SPECIFICATION>...</TERMINAL2 SPECIFICATION>
    </EXECUTION TERMINAL>
    <PURPOSE>...</PURPOSE>
    <EFFICACY>...</EFFICACY>
    <PRESCRIPTION METHOD>...</PRESCRIPTION METHOD>
    <PRECAUTIONS FOR USAGE>...</PRECAUTIONS FOR USAGE>
    <PRESCRIPTION_DIGITAL THERAPEUTICS>EXECUTION BINARY FILE</PRESCRIPTION_DIGITAL THERAPEUTICS>
    <PRESCRIPTION_DIGITAL THERAPEUTICS_EXPIRATION DATE>2022-1-1</PRESCRIPTION_DIGITAL THERAPEUTICS_EXPIRATION DATE>
</xml>
```

FIG. 8

```xml
<xml action="USAGE LOG INFORMATION", name="DIGITAL THERAPEUTICS_A">
    <USER IDENTIFICATION_ID>01010</USER IDENTIFICATION_ID>
    <DISEASE MANAGEMENT CODE>01010</DISEASE MANAGEMENT CODE>
    <LICENSE NUMBER>0010000</LICENSE NUMBER>
    <EXECUTION TERMINAL>
        <TERMINAL2 SPECIFICATION>...</TERMINAL2 SPECIFICATION>
    </EXECUTION TERMINAL>
    <PURPOSE>...</PURPOSE>
    <EFFICACY>...</EFFICACY>
    <PRESCRIPTION METHOD>...</PRESCRIPTION METHOD>
    <PRECAUTIONS FOR USAGE>...</PRECAUTIONS FOR USAGE>
    <USAGE LOG INFORMATION>
        <EXECUTION DATE> JANUARY 01, 2022 12:30</EXECUTION DATE>
        <CONTENT_ASSIGNMENT_DIFFICULTY>CONCENTRATION IMPROVEMENT PROGRAM,DIFFICULTY 2</CONTENT_ASSIGNMENT_DIFFICULTY>
        <DIGITAL THERAPEUTICS_A_COLLECTED INFORMATION>...</DIGITAL THERAPEUTICS_A_COLLECTED INFORMATION>
    <CONTENT_EXECUTION_HISTORY>
        <EXECUTION DATE>JANUARY 01, 2022 12:30</EXECUTION DATE>
        <CONTENT_ASSIGNMENT_DIFFICULTY>CONCENTRATION IMPROVEMENT PROGRAM,DIFFICULTY2</CONTENT_ASSIGNMENT_DIFFICULTY>
        <DIGITAL THERAPEUTICS_A_COLLECTED INFORMATION>...</DIGITAL THERAPEUTICS_A_COLLECTED INFORMATION>
        ...
    </CONTENT_EXECUTION_HISTORY>
    </USAGE LOG INFORMATION>
</xml>
```

FIG. 10

```xml
<xml action="INFORMATION REQUEST_Get or INFORMATION SETTING_Set", DIGITAL THERAPEUTICS_A">
  <USER IDENTIFICATION_ID>01010</USER IDENTIFICATION_ID>
  <DISEASE MANAGEMENT CODE>01010</DISEASE MANAGEMENT CODE>
  <LICENSE NUMBER>0010000</LICENSE NUMBER>
  <EXECUTION TERMINAL>
    <TERMINAL2 SPECIFICATION>…</TERMINAL2 SPECIFICATION>
  </EXECUTION TERMINAL>
  <PURPOSE>…</PURPOSE>
  <EFFICACY>…</EFFICACY>
  <PRESCRIPTION METHOD>…</PRESCRIPTION METHOD>
  <PRECAUTIONS FOR USAGE>…</PRECAUTIONS FOR USAGE>
  <INFORMATION SETTING_Set>
    <CONTROL_CONTENT_ASSIGNMENT_DIFFICULTY>CONCENTRATION IMPROVEMENT PROGRAM, DIFFICULTY2</CONTROL_CONTENT_ASSIGNMENT_DIFFICULTY>
    <CONTROL_EXECUTION TERMINAL>On or Off, …</CONTROL_EXECUTION TERMINAL>
    <CONTROL_PROCESSING NOTIFICATION> TRAINING MONITORING-RELATED NOTIFICATION…</CONTROL_PROCESSING NOTIFICATION>
    <RESTRICTION ON USE> yes or no</RESTRICTION ON USE>
    <RESUME USE> yes or no</RESUME USE>
  </INFORMATION SETTING_Set>
  </INFORMATION SETTING_Set>
  …
  <EXECUTION_CONTENT_ASSIGNMENT_DIFFICULTY></EXECUTION_CONTENT_ASSIGNMENT_DIFFICULTY>
  <EXECUTION TERMINAL_STATUS> On or Off, …</EXECUTION TERMINAL_STATUS>
  …
</INFORMATION REQUEST_Get>
</xml>
```

STORE DEVICE FOR DIGITAL THERAPEUTIC OBJECT AND OPERATION METHOD THEREFOR

CROSS-REFERENCE TO RELATED APPLICATION

This present application claims benefit of priority to Korean Patent Application No. 10-2021-0067630, entitled "APPARATUS AND METHOD FOR PROVIDING ON-LINE STORE SERVICE FOR DIGITAL PHARMACY," filed on May 26, 2021, and Korean Patent Application No. 10-2021-0165883, entitled "APPARATUS AND METHOD FOR PROVIDING ON-LINE STORE SERVICE FOR DIGITAL PHARMACY," filed on Nov. 26, 2021, in the Korean Intellectual Property Office, the entire disclosure of which is incorporated herein by reference.

STATEMENT REGARDING KOREAN GOVERNMENT SUPPORT

The present disclosure was supported at least in part by the Ministry of Science and ICT of the South Korean government for research project, the title of which is DEVELOPMENT OF AUTOMATIC UNTACT PROCESS TECHNOLOGY IN AN PRODUCING ENVIRONMENT OF RECOGNITION REHABILITATION DATA/INFORMATION, (Project Number: 2021070024) conducted by DGIST, and by the Ministry of Education of the South Korean government for research project, the title of which is RESEARCH CENTER FOR OLFACTORY SENSE FUSION (Project Number: 2021030005) conducted by National Research Foundation of Korea.

BACKGROUND OF THE INVENTION

Field of the Invention

The present disclosure relates to a device and method for registering, distributing, and managing digital therapeutics.

Description of the Related Art

Digital therapeutics are intangible software that treats patients with artificial intelligence, virtual reality (VR), chat-bots, games, applications, etc., and undergo, as other drugs, treatment effectiveness verification through clinical trials, government review, prescription of a doctor, and health insurance application.

The Korean Food and Drug Administration (KFDA) recently established guidelines for approval and review of digital therapeutic devices.

Digital therapeutics may be divided into Software as a Medical Device (SaMD) or Software in a Medical Device (SiMD) depending on whether a medical device is installed or not, and may be divided into "address a medical condition", "manage or prevent a medical disorder or disease", "optimize medication", "treat a medical disorder or disease" according to the purpose of treatment.

The recent discussion of digital therapeutics is mostly about the methodology related to a scheme of treating patients by digital therapeutics, and there is a lack of discussion on the methodology for commonly registering, distributing, and managing digital therapeutics developed by various digital therapeutics development (pharmaceutical) companies.

SUMMARY OF THE INVENTION

Therefore, the present disclosure has been made in view of the above problems, and it is an object of the present disclosure to provide a store device for digital therapeutic object for distributing and managing an object including digital therapeutics, and an operation method therefor.

It is another object of the present disclosure to provide a store device for digital therapeutic object capable of recommending a digital therapeutic object, and an operation method therefor.

It is a further object of the present disclosure to provide a technical element of a message for distribution and management of a digital therapeutic object.

It is a further object of the present disclosure to provide a technical element of a message that enables medical staff to access and control a digital therapeutic object installed in a user terminal.

In accordance with an aspect of the present disclosure, the above and other objects can be accomplished by the provision of a digital therapeutic object store device including a processor, a storage unit configured to store a digital therapeutic object, and a memory electrically connected to the processor, at least one piece of code executed by the processor being stored in the memory, in which the memory stores code causing the processor to process an XML-based DPR message requesting any one of registration, update of registration, abandonment of registration, usage, and abandonment of usage of the digital therapeutic object from a first external device during execution through the processor.

In accordance with another aspect of the present disclosure, there is provided a user terminal device using a digital therapeutic object, the user terminal device including a processor, a storage unit configured to download and store a digital therapeutic object, and a memory electrically connected to the processor, at least one piece of code executed by the processor being stored in the memory, in which the memory stores code causing the processor to transmit an XML-based DPR message for requesting usage of the digital therapeutic object to a digital therapeutic object store device during execution through the processor, and the DPR message for requesting usage of the digital therapeutic object includes an XML element capable of expressing any one of a disease code for usage of the digital therapeutic object, a license code of the digital therapeutic object, and a prescription method, which is a control parameter of the digital therapeutic object.

In accordance with a further aspect of the present disclosure, there is provided an operation method for a store device for digital therapeutics, at least some of steps of the operation method being performed by a processor, the operation method including receiving an XML-based DPR message requesting registration of a digital therapeutic object from an external device, and parsing the DPR message requesting registration of the digital therapeutic object, extracting the digital therapeutic object based on an XML element capable of expressing a digital therapeutic object, and storing the digital therapeutic object in a storage device.

In accordance with a further aspect of the present disclosure, there is provided a method of using a digital therapeutic object by a user terminal device, at least some of steps of the method being performed by a processor, the method including transmitting an XML-based DPR message requesting usage of a digital therapeutic object from a store device, and downloading the digital therapeutic object in response to the DPR message requesting usage of the digital therapeutic object, in which the DPR message for requesting usage of the digital therapeutic object includes an XML element capable of expressing any one of a disease code for usage of the digital therapeutic object, a license code of the digital therapeutic object, and a prescription method, which is a control parameter of the digital therapeutic object.

BRIEF DESCRIPTION OF THE DRAWINGS

The above and other objects, features and other advantages of the present disclosure will be more clearly understood from the following detailed description taken in conjunction with the accompanying drawings, in which:

FIGS. 6 to 8 are diagrams for describing a message structure for registering, distributing, or using the digital therapeutic object or requesting information according to an embodiment of the present disclosure;

FIG. 10 is diagram for describing a message structure for requesting information or setting information of the digital therapeutic object according to an embodiment of the present disclosure.

DETAILED DESCRIPTION OF THE INVENTION

Hereinafter, embodiments disclosed in this specification will be described in detail with reference to the accompanying drawings, and the same or similar elements will be given the same reference symbols regardless of reference symbols, and redundant description thereof will be omitted. In the following description, the terms "module" and "unit" for referring to elements are assigned and used interchangeably in consideration of convenience of explanation, and thus, the terms per se do not necessarily have different meanings or functions. Further, in describing the embodiments disclosed in the present specification, when it is determined that a detailed description of a related publicly known technology may obscure the gist of the embodiments disclosed in the present specification, the detailed description thereof will be omitted. In addition, the accompanying drawings are used to help easily understand the embodiments disclosed in this specification, the technical idea disclosed in this specification is not limited by the accompanying drawings, and it should be understood that all alterations, equivalents, and substitutes included in the spirit and scope of the present invention are included.

Although terms including ordinal numbers, that is, "first", "second", etc. may be used herein to describe various elements, the elements are not limited by these terms. These terms are generally only used to distinguish one element from another.

When an element is referred to as being "coupled" or "connected" to another element, the element may be directly coupled or connected to the other element. However, it should be understood that another element may be present therebetween. In contrast, when an element is referred to as being "directly coupled" or "directly connected" to another element, it should be understood that there are no other elements therebetween.

Figure 1:
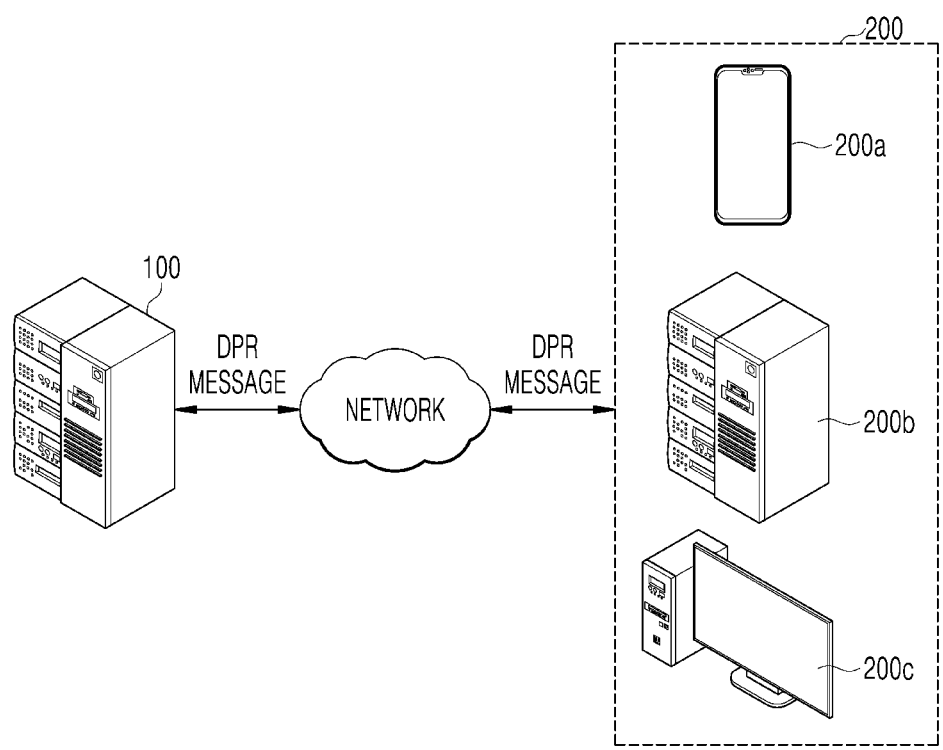
FIG. 1 is a diagram illustrating an environment for operating a digital therapeutic object store device or performing a method according to an embodiment of the present disclosure.

A description will be given of an environment for operating a digital therapeutic object store device 100 according to an embodiment of the present disclosure with reference to FIG. 1.

The environment for performing an operation method for the digital therapeutic object store device or operating the digital therapeutic object store device 100 according to an embodiment of the present disclosure may include the digital therapeutic object store device 100 (hereinafter described as store device 100) and an external device 200.

The external device 200 may be a health insurance server device 200b, a health insurance review and evaluation agency server device 200b, a hospital information device 200b, a digital therapeutics development/pharmaceutical company server device 200b, a health care information server device 200b, a user terminal device 200a, a medical staff terminal 200c, etc.

The external device 200 and the store device 100 may exchange an XML-based DPR message defined in this specification, and in an embodiment, the DPR message may be expressed in the form of Efficient XML Interchange (EXI).

The external device 200 transmits, to the store device 100, a DPR message requesting any one of registration, update of registration, abandonment of registration, usage, and abandonment of usage of a digital therapeutic object including digital therapeutics from the store device 100, and the store device 100 may parse and process the received DPR message.

The storage device 100 may extract necessary information from an XML element of the parsed DPR message, perform processing suitable for the request from the external device 200, and store the digital therapeutic object and the extracted information in the storage device.

Figure 2:
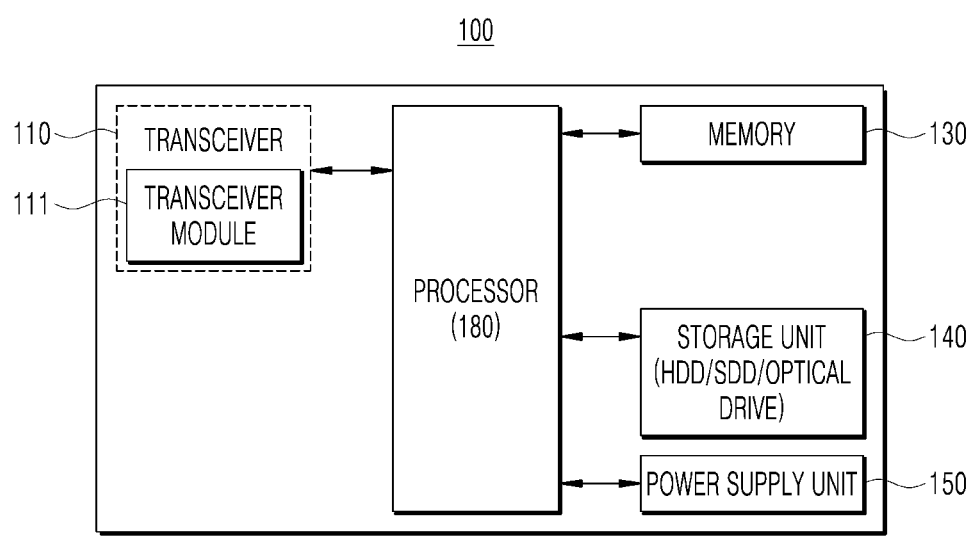
FIG. 2 is a block diagram illustrating a configuration of the digital therapeutic object store device according to an embodiment of the present disclosure.

A configuration of the digital therapeutic object store device 100 according to an embodiment of the present disclosure will be described with reference to FIG. 2.

The store device 100 may include a communication unit 110 for transmitting a DPR message to the external device 200.

The communication unit 110 may include a communication module 111 that is a wireless communication unit or a wired communication unit.

The wireless communication unit may include at least one of a mobile communication module, a wireless Internet module, a short-range communication module, or a location information module.

The mobile communication module transmits and receives a radio signal to and from at least one of a base station, an external terminal, or a server on a mobile communication network constructed according to Long Term Evolution (LTE), which is a communication method for mobile communication.

The wireless Internet module is a module for wireless Internet access and may be provided inside or outside of the store device 100, and it is possible to use Wireless LAN (WLAN), Wi-Fi, Wi-Fi Direct, Digital Living Network Alliance (DLNA), etc. as the wireless Internet module.

The short-range communication module is a module for transmitting and receiving data through short-range communication, and it is possible to use Bluetooth™, Radio Frequency Identification (RFID), Infrared Data Association (IrDA), Ultra-Wideband (UWB), ZigBee, Near Field Communication (NFC), etc. as the short-range communication module.

The storage device 100 may store the received DPR message in a memory 130, parse the DPR message by a processor 180, and store the extracted digital therapeutic object and the extracted information in a storage unit 140. The storage unit 140 includes all types of recording devices in which data is stored. The storage unit 140 may be a storage medium based on a hard disk drive (HDD), a solid state drive (SSD), a silicon disk drive (SDD), a read only memory (ROM), a random access memory (RAM), a CD-ROM, a magnetic tape, a floppy disk, an optical data storage device, etc.

The memory 130 may store code that causes the processor 180 to process an XML-based DPR message requesting any one of registration, update of registration, abandonment of registration, usage, and abandonment of usage of the digital therapeutic object from the external device 200.

In an embodiment, the store device 100 may receive a DPR message, which requests any one of transmission of usage log information of the digital therapeutic object, transmission of usage information of the digital therapeutic object, and setting of a control parameter of the digital therapeutic object, received from the medical staff terminal, and transmit the received DPR message to a user terminal device. In another embodiment, the medical staff terminal may directly transmit a DPR message, which requests any one of transmission of usage log information of the digital therapeutic object, transmission of usage information of the digital therapeutic object, and setting of a control parameter of the digital therapeutic object, to the user terminal device.

The processor 180 may verify whether appropriate information according to an XML element is included in a DPR message for various types of DPR messages. An XML element that defines information necessary for each type of DPR message is described below.

Figure 3:
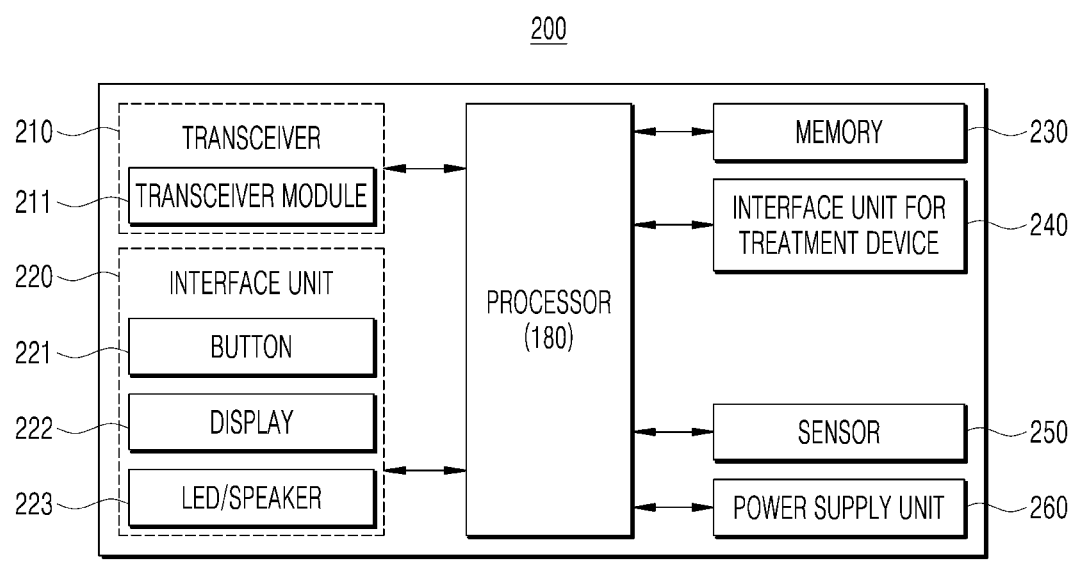
FIG. 3 is a block diagram illustrating a configuration of a user terminal in which a digital therapeutic object is installed and used according to an embodiment of the present disclosure.

A configuration of the user terminal device 200a using the digital therapeutic object according to an embodiment of the present disclosure will be described with reference to FIG. 3. A detailed description of a configuration similar to that of the digital therapeutic object store device 100 will be omitted.

The user terminal device 200a include a communication unit 210 and a communication module 211 for transmitting a DPR message to the store device 100 or the health insurance server device 200b, the health insurance review and evaluation agency server device 200b, the hospital information device 200b, the digital therapeutics development/pharmaceutical company server device 200b, and the health care information server device 200b.

In an embodiment, the user terminal device 200a may include an interface unit 220 including an input unit or an output unit for user input.

The input unit includes a microphone and a user interface (UI) including a touch interface for receiving information from the user, and the UI may include a mouse and keyboard as well as a mechanical or electronic interface implemented in the device. Further, a scheme and a shape thereof are not particularly limited as long as a command of the user can be input. The electronic interface includes a display 222 allowing touch input.

The output unit is for transmitting information to the user by expressing an output of the user terminal device 200a to the outside, and may include a display, an LED, a speaker, etc. for expressing visual output, auditory output, or tactile output.

The user terminal device 200a may include a peripheral device interface unit for data transmission with various types of connected external devices, and may include a memory card port, an external device input/output (I/O) port, etc.

In an embodiment, the user terminal device 200a may download the digital therapeutic object, and transmit the digital therapeutic object to a treatment device in the form of software in a medical device (SiMD) connected to the user terminal device 200a or store the digital therapeutic object in an internal memory 230 to operate as software as a medical device (SaMD). In another embodiment, the digital therapeutic object may be pre-installed in the treatment device in the form of SiMD, and the user terminal device 200a may connect and use the downloaded digital therapeutic object (which may be prescription or usage code) and the digital therapeutic object in the treatment device in the form of SiMD.

In an embodiment, the user terminal device 200a may include a sensing unit 250 including an infrared sensor, an optical heart rate sensor (PPG), an electric heart rate sensor (ECG), a bioelectrical impedance analysis sensor (BIA), etc. for usage of the digital therapeutics. The user terminal device 200a may input data sensed by the sensing unit 250 to the digital therapeutics.

When the user terminal device 200a is used in connection with the treatment device in the form of SiMD, data may be transmitted and received to and from an appropriate interface unit 240 (USB-C cable, dedicated type cable, Bluetooth, wireless interface of LAN, etc.).

In an embodiment, the user terminal device 200a may use the digital therapeutics only at a certain location, and the location information module is a module for acquiring a location of the user terminal device 200a, and may be a global positioning system (GPS) module based on satellite navigation technology or a module for acquiring a location based on wireless communication with a wireless communication base station or a wireless access point. The location information module may include a Wi-Fi module.

In an embodiment, the user terminal device 200a may input data (which may be, for example, bio-information of a user sensed by the sensing unit 250) to a machine learning-based learning model as digital therapeutics, and perform treatment according to an output thereof.

The machine learning-based learning model may include a neural network having a structure of a CNN, a Region based CNN (R-CNN), a Convolutional Recursive Neural Network (C-RNN), a Fast R-CNN, a Faster R-CNN, a Region-based Fully Convolutional Network (R-FCN), You Only Look Once (YOLO), or Single Shot Multibox Detector (SSD).

The learning model may be implemented in hardware, software, or a combination of hardware and software. When a part or the entire learning model is implemented in software, one or more instructions included in the learning model may be stored in a memory.

Figure 4:
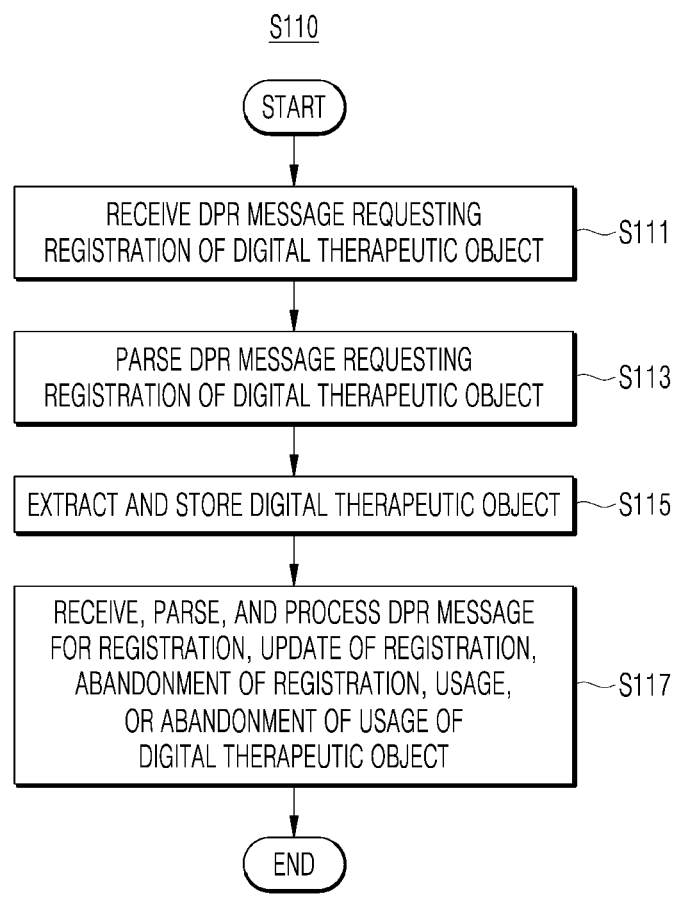
FIG. 4 is a flowchart for describing an operation method for the digital therapeutic object store device according to an embodiment of the present disclosure.

A description will be given of the operation method for the digital therapeutic object store device 100 according to an embodiment of the present disclosure with reference to FIG. 4.

The digital therapeutic object store device 100 may receive an XML-based DPR message requesting registration or update of registration of the digital therapeutic object from any one of the health insurance server device 200b, the health insurance review and evaluation agency server device 200b, the hospital information device 200b, the digital therapeutics development/pharmaceutical company server device 200b, and the health care information server device 200b (S111).

Figure 5:
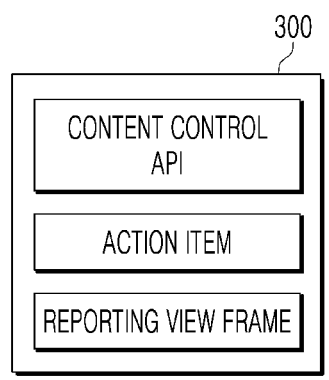
FIG. 5 is a diagram for describing a configuration of the digital therapeutic object according to an embodiment of the present disclosure.

Referring to FIG. 5, a digital therapeutic object 300 may include content used for a digital treatment, a content control API for setting and controlling the content, and a reporting view frame code for displaying a process and result of using the content. The content may include a binary file such as a sound file, or an image or moving image file for presenting a visual or auditory effect to a user who is a patient, a game file, or a digital therapeutics execution file.

In an embodiment, the content control API may include a Set API that performs analysis, processing, and storage commands for a parameter used for content playback or execution, and a Get API for obtaining a parameter used for content or a result of using the content.

In an embodiment, any one of the health insurance server device 200b, the health insurance review and evaluation agency server device 200b, the hospital information device 200b, the digital therapeutics development/pharmaceutical company server device 200b, the health care information server device 200b, and the medical staff terminal 200c may change or process execution parameters of the digital therapeutics of the user or acquire usage results such as log information using the digital therapeutics, a result after usage, and sensing information including bio-information through the content control API of the digital therapeutic object of the user terminal device 200a. Accordingly, unlike conventional digital therapeutics, the digital therapeutic object according to an embodiment of the present invention includes the content control API, so that an authorized external device may control the digital therapeutics appropriately for the user, change a prescription environment, change prescription parameters, or obtain a result thereof, thereby increasing the therapeutic effect of the patient.

The store device 100 may parse the XML-based DPR message illustrated in FIG. 6 requesting registration or update of registration of the digital therapeutic object (S113), extract information according to an XML element included in the message, and store the extracted information in the memory 130 or the storage unit 140 (S115).

The types of XML elements included according to the types of DPR messages may be as shown in <Table 1>.

TABLE 1

|  | Registration (update) | Usage (abandon) | Usage log info | Info request (set) |
|---|---|---|---|---|
| User identification code |  | ○ | ○ | ○ |
| Disease management code | ○ | ○ | ○ | ○ |
| License number (prescription code) | ○ | ○ | ○ | ○ |
| Execution terminal specification | ○ | ○ | ○ | ○ |
| Purpose | ○ | ○ | ○ | ○ |
| Efficacy | ○ | ○ | ○ | ○ |

TABLE 1-continued

|  | Registration (update) | Usage (abandon) | Usage log info | Info request (set) |
|---|---|---|---|---|
| Prescription method | ○ | ○ | ○ | ○ |
| Precautions for usage | ○ | ○ | ○ | ○ |
| Therapeutic object | ○ | ○ |  |  |
| Expiration date of therapeutics |  | ○ |  |  |
| Usage log information |  |  | ○ |  |
| Specific items of information setting |  |  |  | ○ |

For example, the DPR message for registration, update of registration, abandonment of registration, usage, and abandonment of usage of the digital therapeutic object may include an XML element capable of expressing a disease code for usage of the digital therapeutic object and a license code of the digital therapeutic object.

The disease code may be a code such as a disease code according to the International Classification of Diseases (ICD) or a disease code according to the Korean Classification of Diseases (KCD).

The license code may be a code for prescribing the digital therapeutics or applying health insurance similarly to a prescription code of the health insurance review and evaluation agency, etc.

The execution terminal specification may be a type of hardware or software of a terminal capable of executing the digital therapeutics of the digital therapeutic object, a type of the terminal, or a model of the terminal. In an embodiment, the execution terminal specification may include a type or code of a sensor necessary to execute the digital therapeutics. The user terminal device 200a may extract the execution terminal specification according to the XML element of the DPR message and may not execute the digital therapeutics when the execution terminal specification does not conform to a specification of the user terminal device 200a.

The purpose and efficacy are treatment by the digital therapeutics and an effect that may be obtained through the treatment, respectively, and may be a name of the disease, symptoms, and a description of the disease.

The prescription method may be a parameter for implementation of the digital therapeutics. For example, it is possible to include internal parameters for executing or controlling the digital therapeutics such as a display time of a display of a specific image, display illuminance of a display, sound reproduction volume, a reproduction interval of a plurality of sound files, and current strength of a treatment device in the form of SaMD or SiMD, which is an external device.

Precautions for usage may be a description for the usage of the digital therapeutics, such as side effects of the digital therapeutics, a usage time during a day, or the allowed number of times of usage during a day.

The therapeutic object may be an object illustrated in FIG. 5 including the digital therapeutics, and may be in the form of a binary file.

The Expiration date of therapeutics may be the expiration date of the digital therapeutics according to the prescription of the medical staff.

The usage log information may be record information which is a record of usage of the digital therapeutics by the user in the user terminal device 200a, and may include a point in time and time of usage, an ID of the user, parameters of the digital therapeutics, etc.

Specific items of information setting are parameters corresponding to the case where an authorized external device controls the digital therapeutics appropriately for the user, changes the prescription environment, changes the prescription parameter, obtains a result of using the digital therapeutics, or obtains a used parameter. For example, the specific items may include internal parameters for executing or controlling the digital therapeutics such as a display time of a display of a specific image, display illuminance of a display, sound reproduction volume, a reproduction interval of a plurality of sound files, and current strength of a treatment device in the form of SaMD or SiMD, which is an external device. Alternatively, the specific items may be currently set parameters of the digital therapeutics.

The store device 100 may extract data assigned to a required XML element from a DPR message requesting registration or update of registration of the digital therapeutic object, compare the data with a preset item standard, and register the digital therapeutic object in a database, change a prescription period of the registered digital therapeutic object, change a relevant disease management code(disease classification code), update registration information by changing the purpose or efficacy of the digital therapeutics, or abandon the registered digital therapeutics (S117).

The store device 100 may receive, from the user terminal device 200a, a DPR message for usage or abandonment of usage of the digital therapeutic object illustrated in FIG. 7, and may process the DPR message.

The user terminal device 200a may transmit a DPR message for usage of the digital therapeutics to the store device 100 in order to download prescribed digital therapeutics or use the downloaded digital therapeutics, and then acquire a usage right.

In an embodiment, the store device 100 may extract a disease management code, a license number, a prescription method, etc. from the DPR message for usage of the digital therapeutic object, compare the extracted disease management code, license number, prescription method, etc. with a prescription DPR message received from the health insurance server device 200b, the health insurance review and evaluation agency server device 200b, the hospital information device 200b, the digital therapeutics development/pharmaceutical company server device 200b, the health care information server device 200b, or the medical staff terminal 200c, and then grant a usage right.

In another embodiment, the store device 100 may grant a usage right by comparing the specification of the DPR message for usage of the digital therapeutic object or a hash value extracted from a data value of the DPR message with a preset value.

When the prescribed digital therapeutics or the downloaded digital therapeutics expire, the user terminal device 200a may transmit a DPR message for abandonment of the digital therapeutic object to the store device 100 in order to abandon the digital therapeutics, and then abandon the usage right therefor. Alternatively, after an expiration date extracted from the DPR message for usage of the digital therapeutic object, the store device 100 may transmit a DPR message for abandonment of the digital therapeutics to the user terminal device 200a.

The store device 100 or the user terminal device 200a may receive a DPR message for requesting usage log information of the digital therapeutic object illustrated in FIG. 8 from the health insurance server device 200b, the health insurance review and evaluation agency server device 200b, the hospital information device 200b, the digital therapeutics development/pharmaceutical company server device 200b, the health care information server device 200b, or the medical staff terminal 200c, and process the DPR message.

The health insurance server device 200b, the health insurance review and evaluation agency server device 200b, the hospital information device 200b, the digital therapeutics development/pharmaceutical company server device 200b, the health care information server device 200b, or the medical staff terminal 200c may request information such as a point in time (including date) at which the user uses the digital therapeutics, a usage time, a used parameter, or used content through the DPR message for requesting the usage log information.

In an embodiment, the store device 100 may receive a DPR message requesting recommendation of the digital therapeutic object from the medical staff terminal 200c or the hospital information device 200b, and then parse the DPR message, thereby extracting and checking body information, disease information, and symptom information of the patient.

The store device 100 may compare the extracted body information, disease information, and symptom information of the patient with data of a plurality of digital therapeutic objects stored in the storage unit 140, and transmit a license code of the digital therapeutic object conforming to a preset standard to the medical staff terminal 200c or the hospital information device 200b. In this case, a similarity may be calculated by comparing the body information, disease information, and symptom information of the patient with efficacy information or other information of the digital therapeutic object. In this instance, the similarity may use a conventionally known similarity comparison method of text or numeric data, such as the Euclidean distance between values to be compared.

In an embodiment, the DPR message for registration of the digital therapeutic object may include an XML element capable of expressing the gender, age, body mass index (BMI), etc. of a treatment target as a prescription method. The store device 100 may compare the extracted body information of the patient with the gender, age, and BMI described as those of a treatment target of the registered digital therapeutics.

Accordingly, when a plurality of digital therapeutics is registered in the same disease management code or when it is difficult for medical staff to prescribe appropriate digital therapeutics, the patient may be prescribed with reference to the digital therapeutics recommended by the store device 100.

Figure 9:
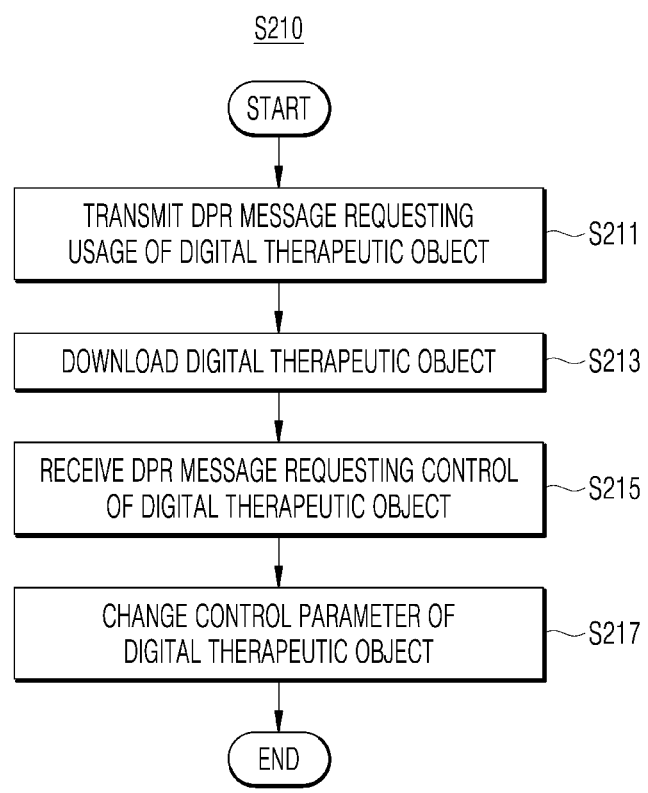
FIG. 9 is a flowchart for describing a method of using the digital therapeutic object by the user terminal using the digital therapeutic object according to an embodiment of the present disclosure.

A description will be given of a method of using the digital therapeutic object by the user terminal device 200a according to an embodiment of the present disclosure with reference to FIG. 9.

The user terminal device 200a may transmit, to the store device 100, an XML-based DPR message requesting usage of the digital therapeutic object prescribed by any one of the health insurance server device 200b, the health insurance review and evaluation agency server device 200b, the hospital information device 200b, the digital therapeutics development/pharmaceutical company server device 200b, and the health care information server device 200b (S211).

In an embodiment, the XML-based DPR message requesting usage of the digital therapeutic object may be as illustrated in FIG. 7.

In an embodiment, the user terminal device 200a may receive a DPR message including the digital therapeutic object from the store device 100 in response to the XML-based DPR message requesting usage of the digital therapeutic object (S213).

In another embodiment, the user terminal device 200a may transmit the XML-based DPR message requesting usage of the digital therapeutic object to the store device 100 (S211) for the digital therapeutic object downloaded from any one of the health insurance server device 200b, the health insurance review and evaluation agency server device 200b, the hospital information device 200b, the digital therapeutics development/pharmaceutical company server device 200b, and the health care information server device 200b (S213), and receive a usage right as a response thereto.

The user terminal device 200a according to an embodiment of the present disclosure may receive a DPR message requesting transmission of usage log information of the digital therapeutic object as illustrated in FIG. 8 or a DPR message requesting transmission of usage information of the digital therapeutic object or setting of a control parameter of the digital therapeutic object as illustrated in FIG. 10 from any one of the store device 100, the health insurance server device 200b, the health insurance review and evaluation agency server device 200b, the hospital information device 200b, the digital therapeutics development/pharmaceutical company server device 200b, the health care information server device 200b, and the medical staff terminal 200c, and parse and process the DPR message.

Referring to FIG. 10, the user terminal device 200a may receive the DPR message requesting transmission of usage information of the digital therapeutic object or setting of a control parameter of the digital therapeutic object.

Upon receiving the DPR message requesting transmission of usage information of the digital therapeutic object, the user terminal device 200a may send information such as a point in time (including date) at which the user uses the digital therapeutics, a usage time, a used parameter, or setting information of used content as a response.

Upon receiving the DPR message for setting of a control parameter of the digital therapeutic object, the user terminal device 200a may change setting of control parameter information such as setting information of content according to a control parameter included in the DPR message.

In an embodiment, any one of the store device 100, the health insurance server device 200b, the health insurance review and evaluation agency server device 200b, the hospital information device 200b, the digital therapeutics development/pharmaceutical company server device 200b, the health care information server device 200b, and the medical staff terminal may perform any one of transmission of usage log information of the digital therapeutic object, transmission of usage information of the digital therapeutic object, and setting of a control parameter of the digital therapeutic object through the content control API of the digital therapeutics installed in the user terminal device 200a.

In an embodiment, the content control API may change the received control parameter using a callback function. For example, the content control API may have the following specifications.

Set(Destination Address(Server/Client), port, DPR, . . . )

Set(Destination Address(Server/Client), port, DPR, FILE*, . . . )

HTTP_FILE_Link Get(Destination Address(Server/Client), port, DPR, . . . )

XML Document Get(Destination Address(Server/Client), port, DPR, . . . )

The digital therapeutic object store device and the operation method therefor according to an embodiment of the present disclosure may provide a centralized environment for distributing and managing digital therapeutics manufactured by various developers.

The digital therapeutic object store device and the operation method therefor according to an embodiment of the present disclosure may provide an environment in which medical staff can easily prescribe various types of digital therapeutics in consideration of symptoms of the patient.

In the technical element of a message of the digital therapeutic object according to an embodiment of the present disclosure, medical staff may access and control the digital therapeutic object installed in the user terminal, thereby changing control setting of the digital therapeutics to be suitable for a condition of the patient.

The present disclosure described above may be implemented as computer-readable code on a medium in which a program is recorded. The computer-readable medium includes all types of recording devices in which data readable by a computer system is stored. Examples of the computer-readable medium include an HDD, an SSD, an SDD, a ROM, a RAM, a CD-ROM, a magnetic tape, a floppy disk, an optical data storage device, etc. In addition, the computer may include a processor of each device.

Meanwhile, the program may be specially designed and configured for the present disclosure, or may be known and available to those skilled in the art of computer software. Examples of the program may include not only machine code generated by a compiler, but also high-level language code that can be executed by a computer using an interpreter, etc.

In the specification of the present disclosure (especially in the claims), the use of the term "the" and similar referential terms may correspond to both the singular and the plural. In addition, when a range is described in the present disclosure, an invention, to which an individual value falling within the range is applied, is included (unless there is a description to the contrary), which is equivalent to describing each individual value included in the range in the detailed description of the invention.

Steps included in the method according to the present disclosure may be performed in an appropriate order unless the order is explicitly stated or there is a description to the contrary. The present disclosure is not limited by the order in which the steps are described. The use of all examples or exemplary terminology (for example, etc.) in the present disclosure is merely for the purpose of describing the present disclosure in detail, and the scope of the present disclosure is not limited by the examples or exemplary terms unless limited by the claims. In addition, those skilled in the art will appreciate that various modifications, combinations and changes may be made according to design conditions and factors within the scope of the appended claims or equivalents thereof.

Therefore, the spirit of the present disclosure should not be limited to the above-described embodiments, and not only the claims described below but also all ranges equivalent to or equivalently changed from the claims fall within the scope of spirit of the present disclosure.

What is claimed is:

1. A store device for digital therapeutic object comprising:
a processor;
a data storage configured to store a digital therapeutic object; and
a memory electrically connected to the processor, at least one code executed by the processor being stored in the memory,
wherein the memory stores the code causing the processor to process an XML-based Digital Pharmaceutical Records or Digital theraPeutics Records (DPR) message requesting any one of registration, update of registration, abandonment of registration, usage, and abandonment of usage of the digital therapeutic object from a first external, and wherein the digital therapeutic object includes:

content used for digital therapeutics;

a content control API configured to set and control the content; and a reporting view frame code configured to display a process and result of using the content, and wherein the content control API of the digital therapeutic object includes a Set API configured to perform analysis, change, processing, and storage commands for a parameter used for the content, and a Get API configured to obtain a parameter used for the content or a result of using the content.

2. The store device according to claim 1, wherein the DPR message for any one of registration, update of registration, abandonment of registration, usage, and abandonment of usage of the digital therapeutic object includes an XML element capable of expressing a disease code and a license code of the digital therapeutic object for usage of the digital therapeutic object.

3. The store device according to claim 1, wherein the DPR message for usage and abandonment of usage of the digital therapeutic object includes an XML element capable of expressing an expiration date of the digital therapeutic object.

4. The store device object according to claim 1, wherein the DPR message for usage or abandonment of usage of the digital therapeutic object includes an XML element capable of expressing a prescription method, which is a control parameter of the digital therapeutic object for therapeutic use.

5. The store device according to claim 1, wherein the memory further stores code causing the processor to parse the DPR message for usage of the digital therapeutic object by a user terminal, and compare the disease code for usage of the digital therapeutic object and the license code of the digital therapeutic object, which are extracted, with information of the digital therapeutic object stored in the data storage.

6. The store device according to claim 1, wherein the memory causes the processor to check body information, disease information, and symptom information of a patient acquired by parsing the DPR message requesting recommendation of the digital therapeutic object received from a second external device, compare efficacy information of a plurality of digital therapeutic objects stored in the data storage with the body information, the disease information, and the symptom information of the patient, and transmit, to the second external device, license codes of a plurality of digital therapeutic objects having similarities, based on comparing the efficacy information of the plurality of digital therapeutic objects, greater than or equal to a preset value.

7. A user terminal device using a digital therapeutic object, the user terminal device comprising:

a processor;

a data storage configured to download and store a digital therapeutic object; and a memory electrically connected to the processor, at least one code executed by the processor being stored in the memory, wherein:

the memory stores the code causing the processor to transmit an XML-based DPR message for requesting usage of the digital therapeutic object to a digital therapeutic object store device; and the DPR message for requesting usage of the digital therapeutic object includes an XML element capable of expressing any one of a disease code for usage of the digital therapeutic object, a license code of the digital therapeutic object, and a prescription method, which is a control parameter of the digital therapeutic object, and wherein the digital therapeutic object includes:

content used for digital therapeutics;

a content control API configured to set and control the content; and a reporting view frame code configured to display a process and result of using the content, and wherein the content control API of the digital therapeutic object includes a Set API configured to perform analysis, change, processing, and storage commands for a parameter used for the content, and a Get API configured to obtain a parameter used for the content or a result of using the content.

8. The user terminal device according to claim 7, wherein the memory further stores the code causing the processor to parse and process the DPR message requesting any one of transmission of usage log information of the digital therapeutic object, transmission of usage information of the digital therapeutic object, and setting of a control parameter of the digital therapeutic object received from a third external device.

9. The user terminal device according to claim 8, wherein the memory further stores the code causing the processor to change a control parameter for therapeutic use of the digital therapeutic object stored in the data storage in response to the DPR message requesting setting of a control parameter of the digital therapeutic object received from the third external device.

10. The user terminal device according to claim 8, wherein the memory further stores code causing the processor to perform processing for a request for any one of transmission of usage log information of the digital therapeutic object, transmission of usage information of the digital therapeutic object, and setting of a control parameter of the digital therapeutic object through a content control API.

11. A method for operating a store device for digital therapeutics, at least some of steps of the operation method being performed by a processor, the operation method comprising:

receiving an XML-based DPR message requesting registration of a digital therapeutic object from an external device; and parsing the DPR message requesting registration of the digital therapeutic object, extracting the digital therapeutic object based on an XML element capable of expressing a digital therapeutic object, and storing the digital therapeutic object in a storage device, and wherein the digital therapeutic object includes:

content used for digital therapeutics;

a content control API configured to set and control the content; and a reporting view frame code configured to display a process and result of using the content, and wherein the content control API of the digital therapeutic object includes a Set API configured to perform analysis, change, processing, and storage commands for a parameter used for the content, and a Get API configured to obtain a parameter used for the content or a result of using the content.

12. The method according to claim 11, further comprising receiving, parsing, and processing the DPR message for requesting any one of update of registration, abandonment of registration, usage, and abandonment of usage of the digital therapeutic object,
   wherein the DPR message for requesting any one of update of registration, abandonment of registration, usage, and abandonment of usage of the digital therapeutic object includes an XML element capable of expressing a disease code and a license code of the digital therapeutic object for usage of the digital therapeutic object.

13. The method according to claim 12, wherein the DPR message for usage and abandonment of usage of the digital therapeutic object includes an XML element capable of expressing an expiration date of the digital therapeutic object.

14. The method according to claim 12, wherein the DPR message for usage or abandonment of usage of the digital therapeutic object includes an XML element capable of expressing a prescription method, which is a control parameter of the digital therapeutic object for therapeutic use.

15. The method according to claim 11, further comprising:
   receiving the DPR message for usage of the digital therapeutic object by a user terminal; and
   parsing the DPR message for usage of the digital therapeutic object to compare a disease code for usage of the digital therapeutic object and a license code of the digital therapeutic object, which are extracted, with information of the digital therapeutic object stored in the storage device.

16. The method according to claim 11, further comprising:
   receiving the DPR message requesting recommendation of the digital therapeutic object from a medical staff terminal;
   checking body information, disease information, and symptom information of a patient acquired by parsing the DPR message requesting recommendation of the digital therapeutic object;
   comparing efficacy information of a plurality of digital therapeutic objects stored in the storage device with the body information, the disease information, and the symptom information of the patient; and
   transmitting, to the medical staff terminal, license codes of a plurality of digital therapeutic objects having similarities, based on the comparing the efficacy information of the plurality of digital therapeutic objects, greater than or equal to a preset value.

17. A method of using a digital therapeutic object by a user terminal device, at least some of steps of the method being performed by a processor, the method comprising:
   transmitting an XML-based DPR message requesting usage of a digital therapeutic object from a store device; and
   downloading the digital therapeutic object in response to the DPR message requesting usage of the digital therapeutic object,
   wherein the DPR message for requesting usage of the digital therapeutic object includes an XML element capable of expressing any one of a disease code for usage of the digital therapeutic object, a license code of the digital therapeutic object, and a prescription method, which is a control parameter of the digital therapeutic object, and
   wherein the digital therapeutic object includes:
   content used for digital therapeutics;
   a content control API configured to set and control the content; and
   a reporting view frame code configured to display a process and result of using the content, and
   wherein the content control API of the digital therapeutic object includes a Set API configured to perform analysis, change, processing, and storage commands for a parameter used for the content, and a Get API configured to obtain a parameter used for the content or a result of using the content.

18. The method according to claim 17, further comprising:
   receiving and then parsing the DPR message requesting setting of a control parameter of the digital therapeutic object received from a third external device; and
   changing a control parameter for therapeutic use of the digital therapeutic object stored in a data storage in response to the DPR message requesting setting of a control parameter of the digital therapeutic object.

* * * * *